United States Patent [19]

Resemann et al.

[11] Patent Number: 5,248,695
[45] Date of Patent: Sep. 28, 1993

[54] SEPARATION OF ENANTIOMERS OF CIMATEROL, (−)-CIMATEROL AND THE USE THEREOF IN ANIMAL FEEDS

[75] Inventors: Wolfgang Resemann; Adolf Durr; Gunther Engelhardt, all of Biberach; John F. Quirke, Bingerbruck, all of Fed. Rep. of Germany

[73] Assignee: Boehringer Ingelheim Vetmedica GmbH, Ingelheim am Rhein, Fed. Rep. of Germany

[21] Appl. No.: 693,760

[22] Filed: Apr. 30, 1991

[30] Foreign Application Priority Data

May 4, 1990 [DE] Fed. Rep. of Germany ....... 4014252

[51] Int. Cl.$^5$ ..................... A01N 37/34; C07C 255/00
[52] U.S. Cl. ..................................... 514/524; 558/422
[58] Field of Search ......................... 558/422; 514/524

[56] References Cited

U.S. PATENT DOCUMENTS

| 4,119,710 | 10/1978 | Engelhardt et al. | 549/442 |
| 4,407,819 | 10/1983 | Kiernan | 424/304 |
| 4,814,350 | 3/1989 | Goidl et al. | 514/524 |

OTHER PUBLICATIONS

Chem. Abstracts; (American Cyanamid) vol. 108, No. 12; 101337u (1988).

*Primary Examiner*—C. Warren Ivy
*Assistant Examiner*—Raymond Covington
*Attorney, Agent, or Firm*—David E. Frankhouser; Alan R. Stempel; Mary-Ellen M. Timbers

[57] ABSTRACT

The invention relates to the separation of enantiomers, of cimaterol, (−)-cimaterol, the addition salts thereof and processes for preparing them and their use in pharmaceutical compositions and animal feeds.

3 Claims, No Drawings

SEPARATION OF ENANTIOMERS OF CIMATEROL, (−)-CIMATEROL AND THE USE THEREOF IN ANIMAL FEEDS

FIELD OF THE INVENTION

The present invention relates to the separation of enantiomers of cimaterol, (-)-cimaterol and the use thereof in pharmaceutical compositions and animal feeds.

BACKGROUND OF THE INVENTION

U.S. Pat. No. 4,119,710 describes inter alia the racemate 1-(4'-amino-3'-cyano-phenyl)-2-isopropylaminoethanol (generic name: cimaterol) and its pharmaceutical properties. Thus, the compounds described in U.S. Pat. No. 4,119,710 have, in addition to their analgesic and uterus-spasmolytic effects and their antispastic effects on the transverse-stripped musculature, in particular $\beta_2$-mimetic and/or $\beta_1$-blocking effects, with one or other effect being dominant depending on the substitution. It is also established in U.S. Pat. No. 4,119,710 that the d(+)compounds have in particular a selective effect on the $\beta_1$-receptors and the 1-(−)-compounds have a preferred effect on the $\beta_2$-receptors.

Moreover, U.S. Pat. No. 4,407, 819, inter alia describes the performance-enhancing effect of cimaterol in animals.

It is also known that, normally, one of the two enantiomers of a racemate is more pharmacologically effective than the other enantiomer.

U.S. Pat. No. 4,119,710 describes two methods of separating the enantiomers of cimaterol, namely:

a) the resolution of a mixture of diastereomeric compounds which are obtained by reacting the corresponding racemate with a chiral acyl group, and subsequently cleaving the chiral acyl group, e.g. the (−)-methylcarbonyl group, or b) the fractional crystallization of a mixture of diastereomeric salts, which are formed by reaction of the racemic base with an optically active auxiliary acid.

Racemate separation by method (a) is not thought to be promising since the cyano group present in cimaterol would be at least partially changed by hydrolysis or hydrogenolysis during the subsequent hydrolytic or hydrogenolytic cleaving of the chiral acyl group which would have to be carried out.

As is shown by the reference example which appears below, the conventional racemate separation, by method (b), does not resolve racemic cimaterol with good yields.

SUMMARY OF THE INVENTION

A first aspect of the invention comprises an improved method for resolving racemic cimaterol into its enantiomers. A second aspect of the invention comprises (−)-cimaterol. Other aspects of the invention comprise pharmaceutical compositions and animal feed compositions comprising (−)-cimaterol.

DETAILED DESCRIPTION OF THE INVENTION

Surprisingly, it has now been found that racemic cimaterol, which may contain one of the desired enantiomers in concentrated form, can be resolved, by dissolving cimaterol and at least 2 equivalents, appropriately from 2 to 7 equivalents, but preferably 2 to 4 equivalents, of an optically active dibasic auxiliary acid such as (−)-0,0'-dibenzoyl-L-tartaric acid, (+)-0,0'-dibenzoyl-D-tartaric acid, (−)-0,0'-ditolyl-L-tartaric acid or (+)-0,0'-ditolyl-D-tartaric acid, keeping within a temperature range which is specific to each auxiliary acid and is preferably above 20° C. but preferably between 25° and 30° C., in a suitable solvent, via the two diastereomeric salts thereof with subsequent liberation of the enantiomeric base. The desired diastereomeric salt is precipitated with a degree of purity of at least ee=90% after a short time, e.g. 1 to 5 minutes, whilst the temperature must not fall below the range which is characteristic of each auxiliary acid. Preferably, the two components are dissolved simultaneously, and obviously a solution of one component can be added to a solution of the other component.

It is particularly advantageous to carry out the racemate separation with 2 to 7 equivalents, preferably with 1 to 3 equivalents of (−)-0,0'-dibenzoyl-L-tartaric acid or (')-0,0'-dibenzoyl-D-tartaric acid as the auxiliary acid at temperatures above 25° C., but preferably in a temperature range between 25° and 30° C. Thus, for example, after 1 mol of cimaterol and 1 mol of (−)-0,0'-dibenzoyl-L-tartaric acid or (+)-0,0'-dibenzoyl-D-tartaric acid have been dissolved in methanol simultaneously, pure (+)-1-(4'-amino-3'-cyano-phenyl)-2-isopropylamino-ethanol-(−)-0,0'-dibenzoyl-L-hydrogen tartrate or (−)-1-(4'-amino-3'-cyano-phenyl)-2-isopropylamino-ethanol-(+)-0,0'-dibenzoyl-D-hydrogen tartrate is obtained, and after a short time, e.g. 1 to 2 minutes, the pure diastereomeric hydrogen tartrate in question begins to crystallize. This salt occurs in a high degree of purity of at least ee=94% even after the first step. If even greater purity is required, the separation process can be repeated once or several times, if necessary, by dissolving the diastereomeric hydrogen tartrate obtained after a single precipitation and recrystallizing it at above 25° C.

The desired pure enantiomeric base is then liberated from the diastereomeric salt thus obtained using a base, preferably dilute ammonia, and the pure base liberated is then isolated by conventional methods.

The enantiomeric bases obtained may, if desired, subsequently be converted into the acid addition salts thereof, more particularly, for pharmaceutical use, into the physiologically acceptable salts thereof with organic or inorganic acids, but preferably with organic acids. Suitable acids include, for example, hydrochloric, hydrobromic, sulfuric, phosphoric, fumaric, succinic, lactic, citric, tartaric or maleic acid.

However, a particularly remarkable feature of the process according to the invention is that, if the temperature is accidentally allowed to fall below the prescribed range, the racemic cimaterol-0,0'-dibenzoyl-L-or cimaterol-0,0'-dibenzoyl-D-hydrogen tartrate obtained by way of example can be converted into the desired pure diastereomeric hydrogen tartrate, after resuspension and heating to above 25° C.

The invention thus also relates to the diastereomeric salts mentioned above, namely (−)-cimaterol or (−)-cimaterol which is substantially optically pure, i.e. has an optical purity of at least ee=90%, preferably 94 to 100%, the acid addition salts thereof, more particularly the physiologically acceptable acid addition salts thereof with organic or inorganic acids, and the use thereof as pharmaceutical compositions and performance enhancers in animals.

The experiments described below show that the L-enantiomer of cimaterol, i.e. (−)-cimaterol (the term (−)-cimaterol denoting the enantiomer which rotates the plane of oscillation of linearly polarized light of the sodium-D-line to the left) is surprisingly the only carrier of the biological effects of cimaterol: I. The two enantiomers of cimaterol were subjected to comparative tests to investigate their β-mimetic effects on the smooth muscle of the bronchus, the skeletal musculate and the fat cells. They were also compared for their acute toxicity.

The β-mimetic effect on the smooth muscle was examined in terms of a broncholytic effect in the test designed by KONSETT and RÖSSLER (Arch. Exp. Path. Pharmakol. 195, 71–74 (1940)) compared with the acetyl choline-induced bronchospasm in guinea-pigs after i.v. administration. From the inhibition of bronchospasm achieved with the various doses of the test substance, an $ED_{50}$ was calculated by linear regression analysis as the dosage which resulted in a 50% inhibition of bronchospasm.

The following Table contains the results found:

| Substance | $ED_{50}$ μg/kg |
| --- | --- |
| (−)-Cimaterol | 0.27 (0.18–0.38) |
| (+)-Cimaterol | 31.30 (5.50–48.30) |

The L-enantiomer is about 100 times more effective on the β-receptors of the bronchus than the corresponding D-enantiomer.

The β-mimetic effect on the skeletal musculature was tested using the method of BOWMAN and NOTT (Pharmacol. Rev. 21, 27 (1969)). This investigates the influence on the tension of the incompletely tetanically contracting M. soleus of anaesthetized cats after i.v. administration.

The results obtained are shown in the following Table:

| Substance | Dose μg/kg | n | Reduction in tension in % x | SD |
| --- | --- | --- | --- | --- |
| Cimaterol | 0.5 | 5 | 38.3 | 10.8 |
| (−)-Cimaterol | 0.5 | 5 | 42.1 | 6.0 |
| (+)-Cimaterol | 50.0 | 5 | 33.7 | 8.0 |

The L-enantiomer of cimaterol is also more than 100 times more effective than the corresponding D-enantiomer on the β-receptors of the skeletal musculature.

The β-mimetic effect on the fat cells was investigated in terms of a lipolytic effect on conscious rabbits after i.v. administration. The changes in the free fatty acids in the rabbit's blood, achieved by means of the various doses of test substances (measured by the method of DUNCOMBE: Biochem. J. 88.8 (1963)) was used to calculate, by linear regression analysis, an $ED_{150}$, i.e. the dose which resulted in a 50% increase in the free fatty acid in the blood.

The findings obtained are shown in the following Table:

| Substance | $ED_{150}$ μg/kg |
| --- | --- |
| (−)-Cimaterol | 0.098 (0.078–0.118) |
| (+)-Cimaterol | 9.770 (7.440–12.700) |

The doses of D-cimaterol needed to achieve a 50% increase in the free fatty acids in the rabbit's blood are about 100 times greater than those of the corresponding L-enantiomer.

The acute toxicity was measured in male and female mice weighing between 20 and 25 g after intravenous administration. An $LD_{50}$ was calculated by sample analysis from the percentage of animals which died within 14 days of being given the substance.

The following Table contains the results:

| Substance | $LD_{50}$ mg/kg |
| --- | --- |
| (−)-Cimaterol | 74.8 (70.6–79.2) |
| (+)-Cimaterol | 86.3 (80.6–92.3) |

2. The performance enhancing effect of (−)-cimaterol was investigated on groups of 10 eight month old lambs (Suffolk×Galway wether lambs), which had been fed for 6 weeks with a feed (dry composition per kg: 145 g of crude protein+70 g of crude fibre+17 g of oil+50 g of crude minerals) to which 2 mg/kg of the test substance had been added. At the same time steps were taken to ensure that the lambs were offered at least 10% excess feed during the experimental period. The lambs were then killed and the following parameters were obtained:

| | Control | (+)-Cimaterol | (−)-Cimaterol | Cimaterol |
| --- | --- | --- | --- | --- |
| Starting weight in kg | 34.4 | 34.8 | 34.2 | 34.9 |
| Final weight in kg | 45.4 | 45.7 | 48.0 | 46.0 |
| Weight gain in g per day | 259 | 268 | 324 | 275 |
| Feed utilization in g of weight gain per kg of feed | 190 | 184 | 220 | 196 |
| Weight of carcass in kg | 22.8 | 22.5 | 24.1 | 24.0 |
| Composition of carcass tissue (without bones) in g per kg: | | | | |
| Water | 501 | 501 | 557 | 556 |
| Fat | 348 | 341 | 252 | 265 |
| Protein | 140 | 151 | 177 | 167 |

As already mentioned above, the biological data given show that, surprisingly, (−)-cimaterol is the sole carrier of the desired effects. However, since the D-enantiomer has the same toxicity as the L-enantiomer, the ratio of use to risk can be improved by a factor of 2 by using L-cimaterol instead of the racemate.

(−)-Cimaterol and the physiologically acceptable acid addition salts thereof are therefore suitable for treating obesity, obstructive lung disorders, allergic bronchial asthma, spastic bronchitis, inflammations or premature labor.

In adults the single dose is between 0.01 and 50 μg, but preferably between 0.01 and 10 μg, twice to four times a day. For this purpose (−)-cimaterol or the physiologically acceptable salts thereof may be incorporated, optionally combined with other active substances, into the conventional galenic preparations such as powders, plain or coated tablets, capsules, suppositories or suspensions.

Furthermore, (−)-cimaterol and the acid addition salts thereof may be used, as mentioned hereinbefore, for treating obese animals such as dogs and, by virtue of their effect of reducing body weight (their lipolytic effect), to reduce undesirable fat deposits in animal farming, i.e. to improve the meat quality of farmed animals such as pigs, cattle, sheep and poultry. The above-mentioned compounds may be administered to the animals by oral or non-oral route, e.g. as a feed additive or by injection or by means of implanted minipumps. The daily dose is between 0.01 and 100 μg/kg, but preferably between 0.01 and 10 μg/kg of body weight.

Furthermore, (−)-cimaterol and the acid addition salts thereof may be used as performance enhancers in animals for promoting and accelerating growth, milk and wool production and in order to improve feed utilization, carcass quality and in order to shift the meat-to-fat ratio in favor of meat. The active substances are used in agricultural, breeding, show and pet animals.

The agricultural and breeding animals include mammals such as cattle, pigs, horses, sheep, goats, rabbits, hares, deer, fur animals such as mink and chinchilla, poultry such as chickens, geese, ducks, turkeys, fish such as carp, trout, salmon, eels, tench, pike, and reptiles such as snakes and crocodiles.

The show animals and pet animals include mammals such as dogs and cats, birds such as parrots and canaries and fish such as ornamental and aquarium fish, e.g. goldfish.

The active substances are used during all the growth and performance phases of the animals, irrespective of the animals' sex. Preferably, the active substances are used during the intensive growth and performance phase. Depending on the type of animal, the intensive growth performance phase lasts from one month to 10 years.

The quantity of active substances administered to the animals in order to achieve the desired effect may vary substantially, thanks to the favorable properties of these active substances. This quantity is preferably from 0.01 to 50 μg/kg, particularly 0.01 to 25 μg/kg of body weight per day. The correct quantity of active substance and the appropriate period of treatment depend in particular on the type of animal, its age, sex, state of health and the manner in which the animals are kept and fed and can easily be determined by anyone skilled in the art.

The active substances are administered to the animals by the usual methods. The method of administration depends in particular on the type of animal, and the behavior and state of health of the animals.

The active substances may be administered once. However, it is also possible to administer the active substances throughout part or all of the growth phase, temporarily or continuously. If they are administered continuously, they may be given one or several times a day at regular or irregular intervals.

The substances are administered by oral or parenteral route in suitable formulations or in pure form. Oral formulations are powders, tablets, granules, drenches, bolis as well as feedstuffs, premixes for feedstuffs, and formulations for administering in drinking water.

The oral formulations contain the active substance in concentrations of 0.01 ppb—100%, preferably 0.01 ppb—10%.

Parenteral formulations are injections in the form of solutions, emulsions, suspensions, as well as implants.

The active substances may be present in the formulations on their own or in admixture with other active substances, mineral salts, trace elements, vitamins, proteins, colorings, fats or flavorings.

The concentration of the active substances in the finished feed is normally about 0.01 ppb to 50 ppm, preferably 0.1 ppb to 10 ppm.

The active substances may be added to the feed as they are or in the form of premixes or feed concentrates.

Thus, the feedstuffs according to the invention contain in addition to the active substance and possibly a conventional vitamin and mineral mixture, for example, for fattening pigs: barley, wheat flour, broad beans, shredded rape extract and edible fat; for broilers: maize, soya bean flour, meatmeal, edible fat and soya oil; for cattle: shredded sugar beet, maize gluten, malt germs, soya bean flour, wheat and molasses and for lambs: barley, soya bean flour, maize and molasses. To this feedstuff, one of the above-mentioned compounds of formula I is added as active substance in a concentration of 0.01 ppb to 0.50%, but preferably from 0.1 ppb to 0.05%, the compound preferably being added in the form of an active substance premix. This premix contains, for example, 5 to 10,000 mg, but preferably 50 to 1,000 mg, expediently in 1,000 g of corn starch.

The Examples which follow are intended to illustrate the invention:

REFERENCE EXAMPLE (−)-1-(4'-Amino-3'-cyano-phenyl)-2-isopropylaminoethanol a)

(−)-1-(4'-Amino-3'-cyano-phenyl)-2-isopropylaminoethanol-(+)-0,0'-dibenzoyl-D-hydrogen tartrate 50.0 g (0.23 mol) of cimaterol and 82.4 g (0.23 mol) of (+)-0,0'-dibenzoyl-D-tartaric acid are dissolved in 500 ml of methanol at ambient temperature. After briefly dissolving, the hydrogen tartrate of the cimaterol crystallizes out. The crystal suspension is stirred for about 2 hours at an internal temperature of 19° to 20° C., then suction filtered and the filter residue is washed with cold methanol and dried at 50° C. until a constant weight is obtained. Yield: 90 g (68.0% of theory based on the racemate used), Melting point of the liberated base: 162.8° C. ee=8 b) 88 g of the hydrogen tartrate obtained in a) are refluxed in 500 ml of methanol until totally dissolved and the clear solution is cooled to an internal flask temperature of about 15° C. The crystals precipitated are stirred for about 2 to 3 hours at 15° to 18° C., suction filtered, washed with cold methanol and dried. Yield: 62 g (70.5% of the material put in), Melting point of the liberated base: 160.9° C. ee=24 c) 60 g of the hydrogen tartrate obtained according to b) are dissolved in 350 ml of methanol analogously to a) at boiling temperature, the crystals are stirred for about 12 hours at 10 to 15° C., suction filtered, washed with cold methanol and dried.

Yield: 34 g (56.7% of the material put in), Melting point of the liberated base: 151.6° C. ee=45

After the second recrystallization, the total yield was only 27.2% of theory, based on the racemate put in, and an enantiomeric excess (ee) of only 45 was obtained. Owing to the substantial waste, crystallization was not continued.

EXAMPLE 1

(−)-1-(4'-Amino-3'-cyano-phenyl)-2-isopropylaminoethanol a) (−)-yl)-2-isopropylamino-ethanol-(+)-0,0'-dibenzoyl-D-hydrogen tartrate 50 g (0.23 mol) of 1-(4'-amino-3'-cyano-phenyl)-2-isopropylamino-ethanol and 82.4 g (0.23 mol) of (+)0,0'-dibenzoyl-D-tartaric acid are dissolved in 500 ml of methanol in a 1 liter three-necked flask at 25° to 28° C. with stirring. After about 1 to 2 minutes, the levorotatory diastereomeric hydrogen tartrate crystallizes out of the clear solution. After about 2 hours' stirring at 25° to 28° C. the crystals are suction filtered, washed with a little methanol and dried at 50° C. in a circulating air dryer. Yield: 44 g (66.5% of theory),
Melting point: 140°–141° C.

b) 42 g of the hydrogen tartrate obtained in Example 1a are dissolved in 550 ml of methanol in a 1 liter three-necked flask at boiling temperature with stirring and the hot solution is filtered clear in a 2 liter filter press using a Seitz-EK filter. The filtrate is evaporated down to about 100 to 150 ml of solution under a weak vacuum and the crystal suspension formed is stirred for about 1 hour at 25° to 28° C. The crystals are suction filtered, washed with a little methanol and dried at 50° C. in a circulating air dryer. Yield: 35.7 g (85% based on the hydrogen tartrate used)
Melting point: 140°–141° C.

c)
(−)-1-(4'-Amino-3'-cyano-phenyl)-2-isopropylaminoethanol 36.0 g of the hydrogen tartrate obtained in Example 1b are added gradually to 50 ml of concentrated ammonia and 150 ml of water at ambient temperature. After 1 hours' stirring the crystal suspension is filtered off, washed thoroughly with deionized water and dried at ambient temperature in a circulating air dryer until a constant weight is obtained.
Yield: 11.7 g (85.6% of theory),
Melting point: 146.5° C.
$[\alpha]_D^{20} = -4.37°$
ee=99.4

EXAMPLE 2

(+)-1-(4'-Amino-3'-cyano-phenyl)-2-isopropylaminoethanol a)
(+)-1-(4'-Amino-3'-cyano-phenyl)-2-isopropylamino-ethanol-(−)-0,0'-dibenzoyl-L-hydrogen tartrate Prepared from 1-(4'-amino-3'-cyano-phenyl)-2-isopropyl-amino-ethanol and (−)-0,0'-dibenzoyl-L-tartaric acid analogously to Example 1a. Yield: 69.8% of theory,
Melting point: 140°–141° C.
b) Purification was continued as in Example 1b.
Yield: 83% based on the hydrogen tartrate used,
Melting point: 140°–141° C.
c) (+)-1-(4'-Amino-3'-cyano-phenyl)-2-isopropylaminoethanol
Prepared analogously to Example 1c.

Yield: 81% of theory,
Melting point: 146.5° C.
$[\alpha]_D^{20} = +4.38°$
ee=98.2

EXAMPLE 3

(+)-1-(4'-Amino-3'-cyano-phenyl)-2-isopropylaminoethanol

The mother liquor obtained from the precipitation according to Example 1a is evaporated to dryness in vacuo and the residue obtained is taken up in 50 ml of concentrated ammonia and 150 ml of water and stirred for 2 hours at about 5° to 10° C. After suction filtering, the filter residue is washed thoroughly with water and dried well in a circulating air dryer at ambient temperature.
Yield: 26.5 g (53% based on the racemate used)
The crude (+)-1-(4'-amino-3'-cyano-phenyl)-2-isopropylamino-ethanol thus obtained is purified with (−)-0,0'-dibenzoyl-L-tartaric acid analogously to Example 2:
a) Yield: 39.7 g (56.8% based on the racemate/enantiomer mixture used),
Melting point: 140°–141° C.
b) Yield: 87% based on the hydrogen tartrate used,
Melting point: 140°–141° C.
c) Yield: 78.5% of theory,
Melting point: 146.5° C.
$[\alpha]_D^{20} = +4.37°$ ee=98

EXAMPLE 4

(−)-1-(4'-Amino-3'-cyano-phenyl)-2-isopropylaminoethanol 50 g of (−)-1-(4'-amino-3'-cyano-phenyl)-2-isopropylamino-ethanol-(+)-0,0'-dibenzoyl-L-hydrogen tartrate (prepared according to Reference example a), melting point of the liberated base: 162.8° C.; ee=8) are suspended with 500 ml of methanol and stirred for 1 hour at an internal flask temperature of about 28° C. The mixture is then suction filtered, washed with a little methanol and dried at 50° C. until a constant weight is obtained. Yield: 28.0 g (56% based on the racemate/enantiomer mixture).
The hydrogen tartrate thus obtained is liberated analogously to Example 1c) using dilute ammonia.
Yield: 9.14 g (86% of theory),
Melting point: 145° C.
$[\alpha]_D^{20} = -4.37°$ ee=98

EXAMPLE 5

| Tablets containing 2 μg of (−)-cimaterol | |
|---|---|
| Composition: 1 tablet contains: | |
| Active substance | 0.002 mg |
| Lactose | 82.498 mg |
| Potato starch | 33.000 mg |
| Polyvinylpyrrolidone | 4.000 mg |
| Magnesium stearate | 0.050 mg |
| | 120.000 mg |

Method of preparation:
The active substance and polyvinylpyrrolidone are dissolved in ethanol. The mixture of lactose and potato starch is uniformly moistened with the active substance/granulating solution. Moist screening is carried out with a 1.5 mm mesh screen. The mixture is then dried at 50° C. and dry screening is carried out with a 1.0 mm mesh screen. The granules thus obtained are mixed with magnesium stearate and compressed into tablets.

Weight of tablet: 120 mg
Punch: 7 mm, flat

EXAMPLE 6

| Coated tablets containing 1 µg of (−)-cimaterol | |
|---|---|
| Composition: | |
| 1 tablet contains: | |
| Active substance | 0.001 mg |
| Lactose | 82.499 mg |
| Potato starch | 33.000 mg |
| Polyvinylpyrrolidone | 4.000 mg |
| Magnesium stearate | 0.050 mg |
| | 120.000 mg |

Method of preparation:
Tablet cores analogously to the tablets in Example 5.
Weight of core: 120 mg
Punch: 7 mm, convex
The cores are coated by known methods with a coating consisting essentially of sugar and talc. The finished coated tablets are polished with beeswax.
Weight of coated tablet: 200.0 mg

EXAMPLE 7

| Oblong gelatine capsules containing 1 µg of (−)-cimaterol | |
|---|---|
| Composition: | |
| 1 tablet contains: | |
| Active substance | 0.001 mg |
| Lactose | 59.999 mg |
| Corn starch | 60.000 mg |
| | 120.000 mg |

Method of preparation:
The active substance is intensively mixed with lactose and corn starch and packed into suitably sized oblong gelatine capsules.
Capsule contents: 120.0 mg

EXAMPLE 8

| Ampoules containing 2 µg of (−)-cimaterol per 2 ml | |
|---|---|
| Composition: | |
| 1 ampoule contains: | |
| Active substance | 0.002 mg |
| Citric acid | 2.500 mg |
| Sodium hydrogen phosphate | 7.500 mg |
| Common salt | 4.600 mg |
| Water for ampoules to | 2.000 ml |

Method of preparation:
The active substance, buffer substances and common salt are dissolved in water for ampoules and then filtered to remove any pathogens.
Packaging: in brown 2 ml ampoules under protective gas (N₂)
Sterilization: 20 minutes at 120° C.

EXAMPLE 9

| Suppositories containing 2.5 µg of (−)-cimaterol | |
|---|---|
| Composition: | |
| 1 suppository contains: | |
| Active substance | 0.025 mg |
| Suppository mass (e.g. Witepsol W 45) | 1,699.975 mg |
| | 1,700.000 mg |

Method of preparation:
The finely powdered active substance is stirred into the molten suppository mass, which has been cooled to 40° C., by means of an immersion homogenizer and at 37° C. the mass is poured into slight chilled molds.
Weight of suppository: 1.7 g

EXAMPLE 10

| Syrup containing 2 µg of (−)-cimaterol per 5 ml | | |
|---|---|---|
| Composition: | | |
| 100 ml of syrup contains: | | |
| Active substance | 0.04 | mg |
| Benzoic acid | 0.10 | g |
| Tartaric acid | 1.00 | g |
| Sugar | 50.00 | g |
| Orange flavor | 1.00 | g |
| Red food coloring | 0.05 | g |
| Distilled water to | 100.00 | ml |

Method of preparation:
About 60 g of distilled water are heated to 80° C. and the benzoic acid, tartaric acid, active substance, coloring and sugar are successively dissolved therein. After the solution has been cooled to ambient temperature the flavoring is added and the mixture is made up to the volume specified. The syrup is filtered.

EXAMPLE 11

| Aerosol spray delivering 1 µg of (−)-cimaterol per activation | |
|---|---|
| Composition: | |
| Active substance | 0.00025 mg |
| Soya lecithin | 0.05000 mg |
| Propellant gas mixture 11/12/114 (23:54:23) | 69.94975 mg |
| | 70.00000 mg |

EXAMPLE 12

| Aerosil spray delivering 1 µg of (−)-cimaterol per activation | |
|---|---|
| Composition: | |
| Active substance | 0.00025 mg |
| 99.9% pure ethanol | 0.87500 mg |
| Propellant gas mixture 11/12/114 (23:54:23) | 69.12475 mg |
| | 70.00000 mg |

EXAMPLE 13

| Solution for inhalation containing 59 mg of (−)-cimaterol per 100 ml | |
|---|---|
| Composition: | |
| Active substance | 0.59 mg |
| Sodium chloride | 900.00 mg |
| Benzalkonium chloride | 25.00 mg |

-continued

| Solution for inhalation containing 59 mg of (−)-cimaterol per 100 ml | |
| --- | --- |
| Composition: | |
| Distilled water to | 100.00 ml |

Method of preparation:
The active substance, common salt and benzalkonium chloride are dissolved in distilled water and then filtered to remove any pathogens.

EXAMPLE 14

| Complete food II for fattening pigs | |
| --- | --- |
| Barley | 379 g/kg |
| Wheat flour | 200 g/kg |
| Manioc flour | 135 g/kg |
| Broad beans | 100 g/kg |
| Shredded rape extract | 100 g/kg |
| Edible fat | 65 g/kg |
| Lysine-rich mineral feed for pigs | 20 g/kg |
| Active substance premix | 1 g/kg |

After being carefully mixed in the quantities specified these components yield 1 kg of feed.

The 1 g of active substance premix contains for example 2 mg of active substance and 0.998 g of corn starch.

EXAMPLE 15

| Fattening feed II for broilers | |
| --- | --- |
| Maize | 634 g/kg |
| Soya bean flour | 260 g/kg |
| Meatmeal | 40 g/kg |
| Edible fat | 25 g/kg |
| Soya oil | 17 g/kg |
| Bicalcium phosphate | 12 g/kg |
| Calcium carbonate | 6 g/kg |
| Vitamin/mineral mix | 5 g/kg |
| Active substance premix | 1 g/kg |

After being carefully mixed in the quantities specified, these components yield 1 kg of feed.

The 1 g of active substance premix contains for example 1 mg of active substance and 0.999 g of corn starch.

EXAMPLE 16

| Concentrated feed for cattle | |
| --- | --- |
| Shredded sugar beet | 600.0 g/kg |
| Maize gluten | 100.0 g/kg |
| Malt germs | 50.0 g/kg |
| Soya bean flour | 35.0 g/kg |
| Wheat | 119.0 g/kg |
| Molasses | 60.0 g/kg |
| Feed phosphates | 12.0 g/kg |
| Calcium carbonate | 2.5 g/kg |
| Salt | 5.0 g/kg |
| Minerals | 10.0 g/kg |
| Vitamin premix | 5.5 g/kg |
| Active substance premix | 1.0 g/kg |

When carefully mixed in the quantities specified, these components yield 1 kg of feed.

The 1 g of active substance premix contains for example 2 mg of active substance and 0.998 g of corn starch.

EXAMPLE 17

| Fattening feed for lambs | |
| --- | --- |
| Barley | 690 g/kg |
| Soya bean flour | 100 g/kg |
| Maize | 159 g/kg |
| Molasses | 30 g/kg |
| Vitamin/mineral mix | 20 g/kg |
| Active substance premix | 1 g/kg |

When carefully mixed in the quantities specified, these components yield 1 kg of feed.

The 1 g of active substance premix contains for example 2 mg of active substance and 0.998 g of corn starch.

What is claimed is:
1. (−)-1-(4'-Amino-3'-cyano-phenyl)-2-isopropylamino-ethanol, having an optical purity of at least ee=90% or a physiologically acceptable acid addition salt thereof.
2. The compound according to claim 1, having an optical purity of at least ee=94%.
3. A method for reducing fat deposits in an animal, which method comprises administering to such animal a lipolytic amount of the compound according to claim 1.

* * * * *